United States Patent
Haulon et al.

(10) Patent No.: US 11,173,024 B2
(45) Date of Patent: Nov. 16, 2021

(54) BRANCHED FROZEN ELEPHANT TRUNK DEVICE AND METHOD

(71) Applicant: Cook Medical Technologies LLC, Bloomington, IN (US)

(72) Inventors: Stephan Haulon, Lille (FR); Jarin A. Kratzberg, Lafayette, IN (US); Kevin D. Wilger, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 360 days.

(21) Appl. No.: 15/997,075

(22) Filed: Jun. 4, 2018

(65) Prior Publication Data

US 2019/0365523 A1 Dec. 5, 2019

(51) Int. Cl.
*A61F 2/06* (2013.01)
*A61F 2/07* (2013.01)
(Continued)

(52) U.S. Cl.
CPC .................. *A61F 2/06* (2013.01); *A61F 2/07* (2013.01); *A61F 2/954* (2013.01); *A61F 2/97* (2013.01);
(Continued)

(58) Field of Classification Search
CPC ........ A61F 2/06; A61F 2/07; A61F 2002/061; A61F 2002/065; A61F 2002/067; A61F 2/954; A61F 2/97; A61F 2/064
See application file for complete search history.

(56) References Cited

U.S. PATENT DOCUMENTS

| 5,591,226 A | 1/1997 | Trerotola |
| 5,984,955 A | 11/1999 | Wisselink |

(Continued)

FOREIGN PATENT DOCUMENTS

| EP | 1847234 A1 | 10/2007 |
| WO | WO 01/28453 A2 | 4/2001 |

(Continued)

OTHER PUBLICATIONS

Extended European Search Report for corresponding EP Application No. 19178291.1, dated Oct. 24, 2019, 8 pages.

(Continued)

*Primary Examiner* — Katrina M Stransky
(74) *Attorney, Agent, or Firm* — Crowell & Moring LLP

(57) ABSTRACT

An endoluminal prosthesis system for being deployed in a patient's aorta near the heart includes a graft having a tubular body with a lumen extending from proximal end configured to be deployed near a patient's heart to a distal end configured to be deployed away from the patient's heart. A collar around the graft is sized and configured to be sutured to a patient's aorta. Passageways in the middle portion of the graft permit fluid communication from the lumen of the graft to an exterior of the graft. A respective bridging branch is disposed at each of the passageways, each of the bridging branches having an inner opening and an outer opening so that the bridging branches provide fluid communication from the lumen of the graft to the exterior of the graft. A respective bridging graft is sized and arranged to mate with each of the bridging branches.

21 Claims, 14 Drawing Sheets

(51) Int. Cl.
 *A61F 2/954* (2013.01)
 *A61F 2/97* (2013.01)
(52) U.S. Cl.
 CPC ... *A61F 2002/061* (2013.01); *A61F 2002/065* (2013.01); *A61F 2230/0041* (2013.01)

(56) References Cited

U.S. PATENT DOCUMENTS

| | | | |
|---|---|---|---|
| 6,773,457 | B2 | 8/2004 | Ivancev et al. |
| 8,002,816 | B2 | 8/2011 | Greenberg |
| 8,128,680 | B2 | 3/2012 | Arnault De La Menardiere |
| 8,287,586 | B2 | 10/2012 | Schaeffer |
| 8,915,956 | B2 | 12/2014 | Schaeffer et al. |
| 9,011,517 | B2 * | 4/2015 | Hartley ............... A61F 2/07 623/1.35 |
| 9,044,311 | B2 | 6/2015 | Rasmussen et al. |
| 9,649,188 | B2 | 5/2017 | Hartley |
| 9,662,196 | B2 | 5/2017 | Roeder et al. |
| 9,848,977 | B2 | 12/2017 | Rasmussen et al. |
| 9,993,330 | B2 | 6/2018 | Roeder |
| 10,188,502 | B2 | 1/2019 | Rasmussen et al. |
| 2006/0276883 | A1 | 12/2006 | Greenberg |
| 2007/0010873 | A1 * | 1/2007 | Neri ............... A61F 2/06 623/1.34 |
| 2008/0264102 | A1 | 10/2008 | Berra |
| 2009/0093873 | A1 * | 4/2009 | Navia ............... A61F 2/07 623/1.23 |
| 2010/0036401 | A1 * | 2/2010 | Navia ............... A61F 2/064 606/155 |
| 2010/0042201 | A1 * | 2/2010 | Sherif ............... A61F 2/07 623/1.13 |
| 2011/0288627 | A1 * | 11/2011 | Hartley ............... A61F 2/07 623/1.13 |
| 2012/0158121 | A1 | 6/2012 | Ivancev |
| 2013/0166015 | A1 | 6/2013 | Roeder |
| 2013/0218257 | A1 * | 8/2013 | Sun ............... A61F 2/07 623/1.13 |
| 2017/0273809 | A1 | 9/2017 | Marmur |

FOREIGN PATENT DOCUMENTS

| | | |
|---|---|---|
| WO | WO 2005/046526 | 5/2005 |
| WO | WO 2012/095504 A1 | 7/2012 |
| WO | WO 2014/163957 A1 | 10/2014 |
| WO | WO 2016/098113 | 6/2016 |
| WO | WO 2018/032358 A1 | 2/2018 |
| WO | WO 2018/046917 | 3/2018 |
| WO | WO 2018/060716 A1 | 4/2018 |

OTHER PUBLICATIONS

Extended European Search Report for corresponding EP Application No. 19178293.7, dated Oct. 25, 2019, 9 pages.
Product Brochure by JOTEC GmbH, Hechingen, Germany, "E-Vita Open Plus Hybrid Stent Graft System," 5 pages, http://www.jotec.com/en/products/thoracic-stent-grafts/e-vita-open-plus.html.
Product Brochure by Vascutek Terumo, Scotland, United Kingdom, "Thoraflex Hybrid Plexus" and "Thoraflex Hybrid Ante-Flo," 7 pages, http://www.vascutek.com/thoraflex-hybrid/.
Partial European Search Report for EP Application No. 19178289.5, dated Oct. 23, 2019, 13 pages.
Extended European Search Report for EP Application No. 19178289.5, dated Jan. 23, 2020, 11 pages.
Examination Report for EP Application No. 19178289.5, dated Nov. 4, 2020, 4 pages.
Examination Report for EP Application No. 19178291.1, dated Nov. 4, 2020, 6 pages.

* cited by examiner

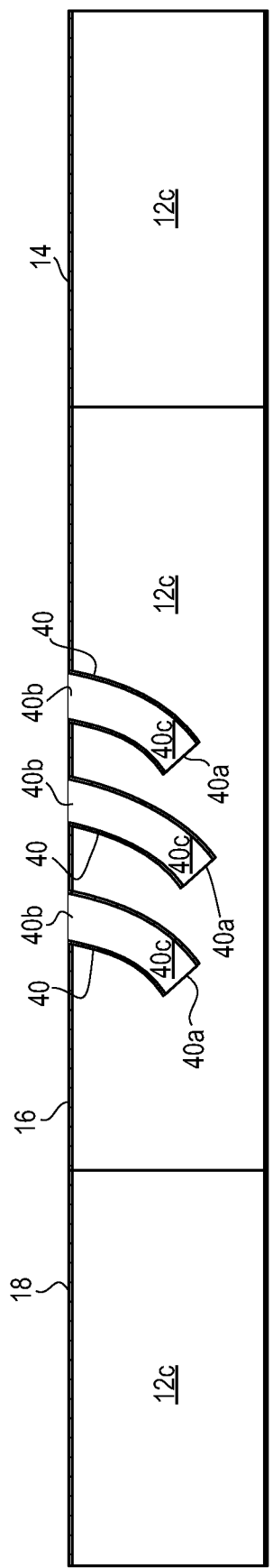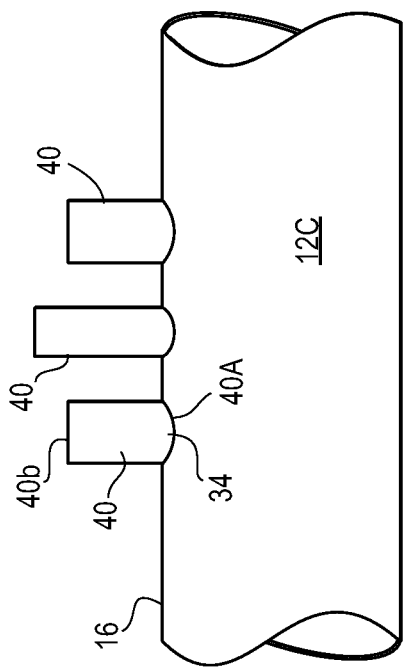

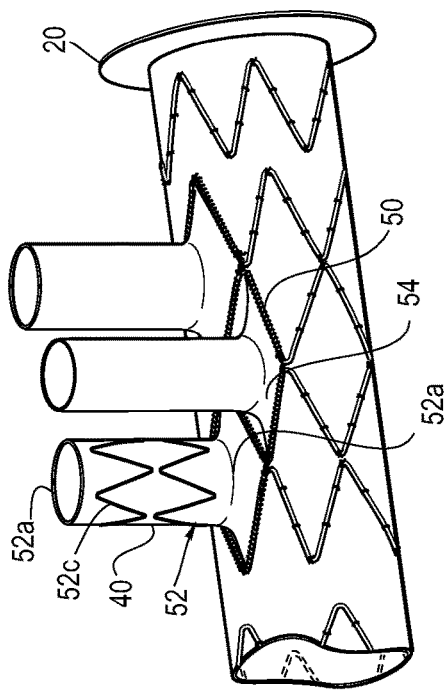
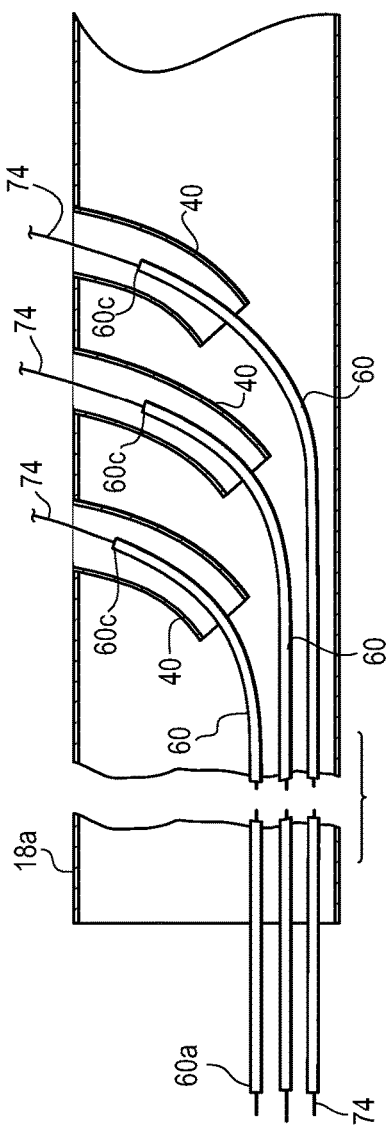
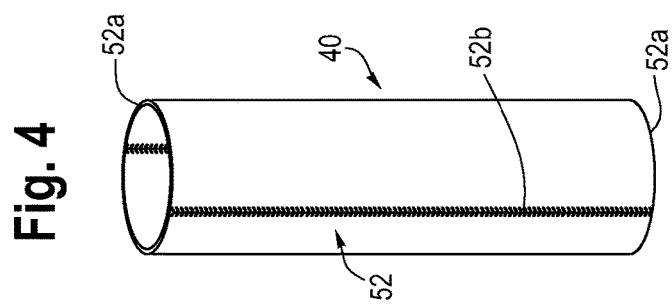

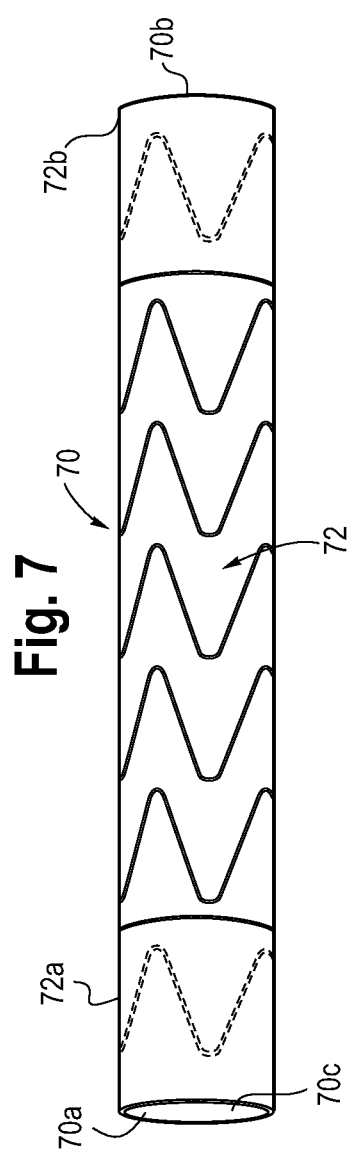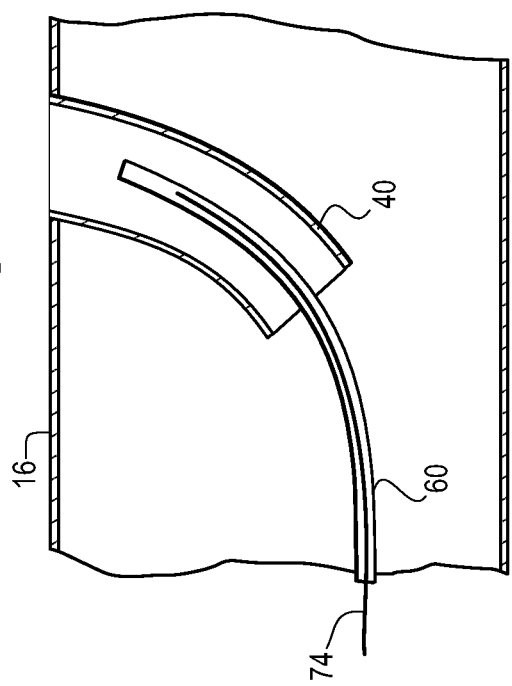

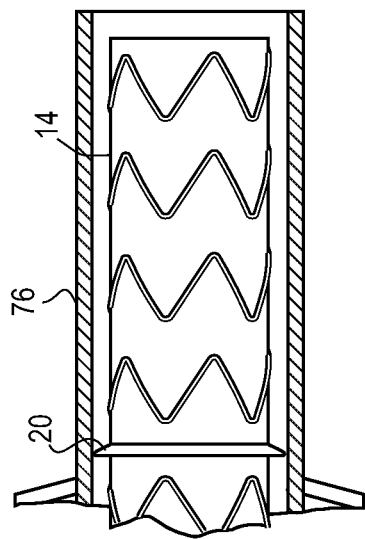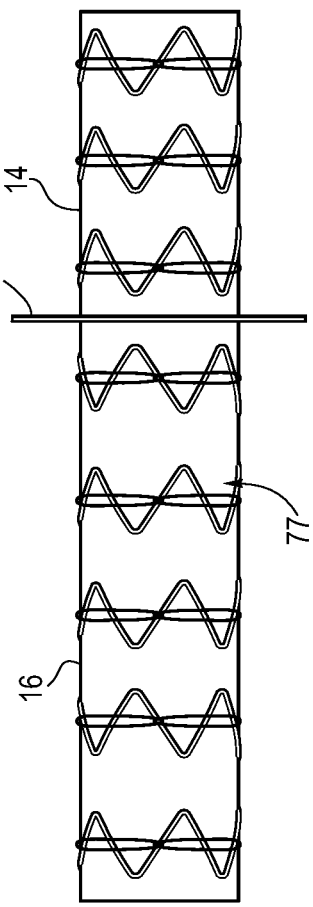

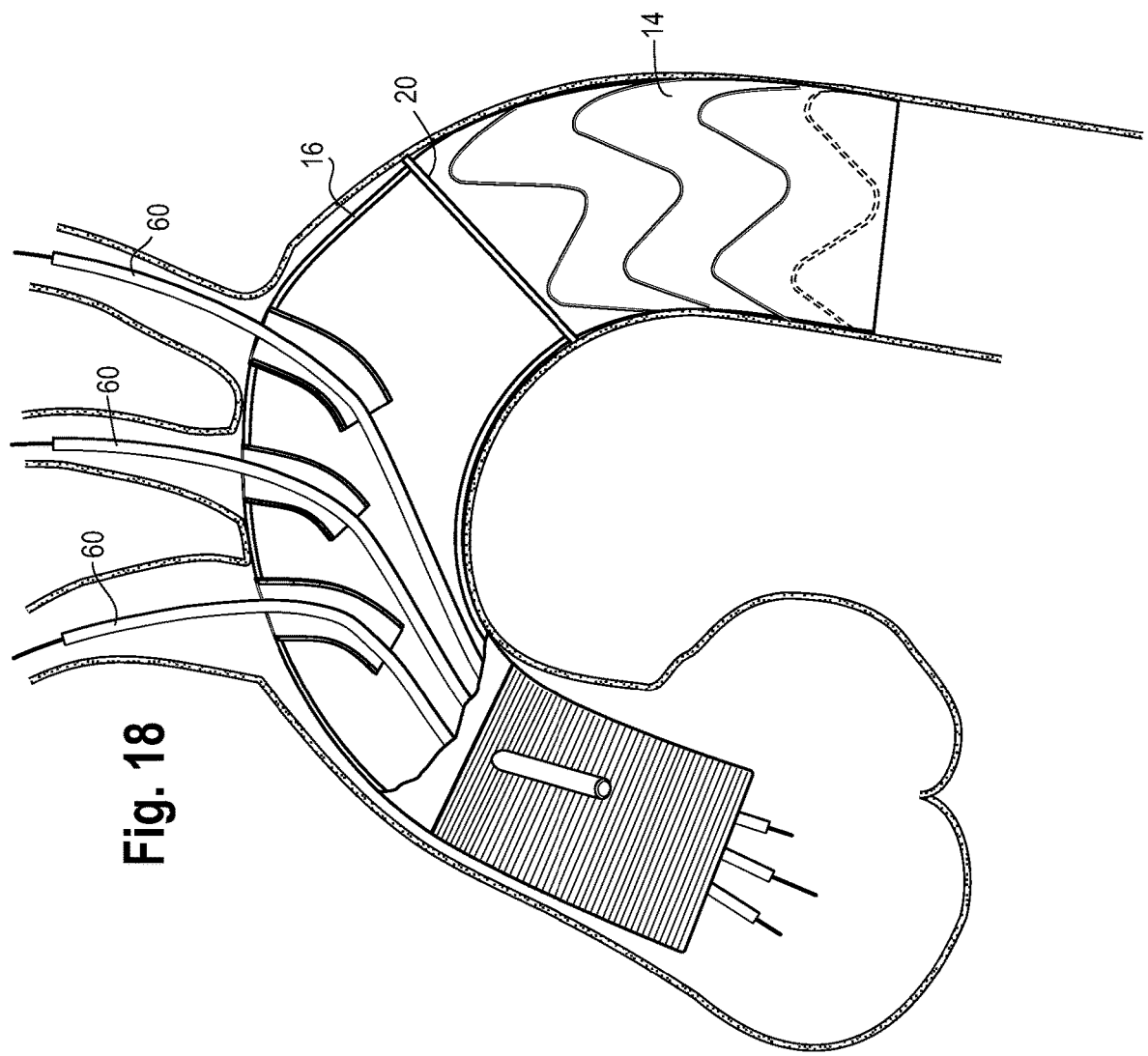

BRANCHED FROZEN ELEPHANT TRUNK DEVICE AND METHOD

TECHNICAL FIELD

This invention relates to medical devices for implantation within the human or animal body for treatment of endovascular disease. More particularly, the invention relates to a prosthesis for treating an aorta of a patient.

BACKGROUND OF THE INVENTION

Endovascular methods have been proposed for treatment of aneurysms of the aorta, particularly when an aneurysm is adjacent the aorta bifurcation. But when an aneurysm occurs higher up in the aorta, for example, in the region of the descending aorta adjacent the thoracic arch or in the ascending aorta, endovascular techniques for treating these aneurysms are somewhat more difficult because of the arched nature of the thoracic arch, the existence of major arteries in the region, and the proximity to the heart.

Generally, operations to treat aneurysms that include the ascending aorta or the arch have been done by open chest surgery. Such surgery generally involves surgical replacement of a portion of the aorta with a tubular prosthesis. The surgery is a high risk procedure. Two foremost reasons for the risk associated with the procedure are difficulty of accessing the site of treatment and the potential for neural ischemia.

In dealing with aortic arch aneurysms, procedural risk is greatly increased by inclusion of the brachiocephalic vessels and the aorta distal to the arch. The difficulty of the procedure also may be exacerbated by the necessity to reconnect the left common carotid and left subclavian arteries to the tubular prosthesis after replacing a portion of the aorta.

One method for treating aortic arch aneurysms includes the use of what is known as a frozen elephant trunk. In this approach, a prosthesis is implanted within the aortic arch that is sutured to create a plurality of anastomoses between the prosthesis and the adjacent tissue.

In one approach, the patient is placed on cardiopulmonary bypass. The descending and ascending aorta are transected, giving the surgeon access to the aorta. The elephant trunk prosthesis is placed within the aorta, with a distal end of the prosthesis being released in the distal aorta. This portion of the prosthesis is known as the frozen trunk.

The prosthesis and graft thereof are sutured to the distal aorta to create a distal anastomosis at the descending transection site. Following this anastomosis, the graft is sutured to the innominate, left common carotid, and left subclavian artery to create an anastomosis at these branch vessels. Finally, the proximal end of the graft is sutured to the ascending aorta to create another anastomosis.

The above frozen elephant trunk procedure has its drawbacks. In particular, the quantity and difficulty of suturing each anastomosis presents challenges. Each anastomosis can require approximately half an hour of operating time. This results in a prolonged period of time for the patient on cardiopulmonary bypass and consequently an increased morbidity for the patient.

Although surgical techniques have been successfully demonstrated to repair arch aneurysms, such techniques are highly invasive and thus limited in utility, especially in high-risk patients.

SUMMARY

According to a first aspect of the present invention, an endoluminal prosthesis system for being deployed in a patient's aorta near the heart includes a graft having a tubular body with a lumen extending from proximal end configured to be deployed near a patient's heart to a distal end configured to be deployed away from the patient's heart. A collar around the graft is sized and configured to be sutured to a patient's aorta. Passageways in the middle portion of the graft permit fluid communication from the lumen of the graft to an exterior of the graft. A respective bridging branch is disposed at each of the passageways, each of the bridging branches having an inner opening and an outer opening so that the bridging branches provide fluid communication from the lumen of the graft to the exterior of the graft. A respective bridging graft is sized and arranged to mate with each of the bridging branches.

The middle portion of the graft may be stented, for example by including a plurality of reinforcing members, each of the reinforcing members respectively surrounding one of the passageways.

The proximal portion may be unstented and include a side branch extending radially outward from the proximal portion and providing fluid communication into the lumen of the graft.

The endoluminal prosthesis system may further include a plurality of catheters extending into the proximal end and further into a respective one of the plurality of bridging branches, wherein the catheters are movable out of the bridging branches.

The system may also include a plurality of wires sized and configured to be extended through the bridging branches and the proximal end.

In one embodiment, the outer opening of each of the bridging branches is attached at a sidewall of the middle portion, and the inner opening of each of the bridging branches is disposed within the lumen of the graft.

In another embodiment, the inner opening of each of the bridging branches is attached at a sidewall of the middle portion, and the outer opening is disposed outside of the lumen of the graft.

For facilitating the delivery and the placement of the bridging branches in the branch vessels, each of the bridging branches may be pivotable relative to the tubular body of the graft at an attachment interface between the tubular body and the bridging branch.

According to another aspect of the invention, an endoluminal prosthesis system for being deployed in a patient's aorta near the heart comprises a graft having a tubular body with a proximal end and a distal end, where the proximal end is an end configured to be deployed near a patient's heart and the distal end is an end configured to be deployed away from the patient's heart. The tubular body has a lumen extending from the proximal end to the distal end. A proximal portion of the graft includes the proximal end; a distal portion of the graft includes the distal end; and a middle portion of the graft extends from the proximal portion to the distal portion. A plurality of bridging branches is attached to a wall of the tubular graft. Each of the bridging branches has an inner opening and an outer opening, wherein the bridging branches provide fluid communication from the lumen of the graft to the exterior of the graft. The system further includes a plurality of catheters extending through the inner openings of the bridging branches and through the distal end of the graft.

The system may further comprise a plurality of bridging grafts sized and arranged to mate respectively with one of the bridging branches.

A plurality of preloaded wires extending into the catheters and configured to be extended out of the catheters and out of the outer opening of the bridging branches may be included in the system.

For ease of delivery, the distal portion may a compressed delivery configuration and an expanded deployed configuration and be expandable into the deployed configuration separately from the middle portion.

Similarly, the middle portion may a compressed delivery configuration and an expanded deployed configuration.

In one example, the inner openings of the bridging branches are disposed inside the lumen.

Alternatively, the inner openings of the bridging branches are attached to a wall of the middle portion and the bridging branches are pivotable relative to graft.

The presently preferred embodiments, together with further advantages, will be best understood by reference to the following detailed description taken in conjunction with the accompanying drawings. The drawings are provided herewith for illustrative purposes and are not intended to limit the scope of the present invention.

BRIEF DESCRIPTION OF THE DRAWINGS

In the drawings,

FIG. 2 shows a schematic cross-sectional view of the prosthesis of FIG. 1;

FIG. 3 shows a partial perspective view of a second example of an endoluminal prosthesis with external bridging branches;

FIG. 4 shows a detail of a bridging branch;

FIG. 5 shows a further example of an endoluminal prosthesis;

FIG. 6 shows a cross-sectional view of an endoluminal prosthesis with branch catheters and route wires;

FIG. 7 shows an example of a graft extension;

FIG. 8 shows a cross-sectional detail of an endoluminal prosthesis with a branch catheter and a route wire;

FIG. 10 shows a partial cross-sectional view of a restraining sheath surrounding a distal portion of an endoluminal prosthesis;

FIG. 11 shows a distal portion of an endoluminal prosthesis with diameter-reducing ties; and FIGS. 12, 13, 14, 15, 15A, 16, 17, and 18 show various successive stages of delivering an endoluminal prosthesis into a patient's aortic arch and branch vessels.

DETAILED DESCRIPTION

Figure 1:
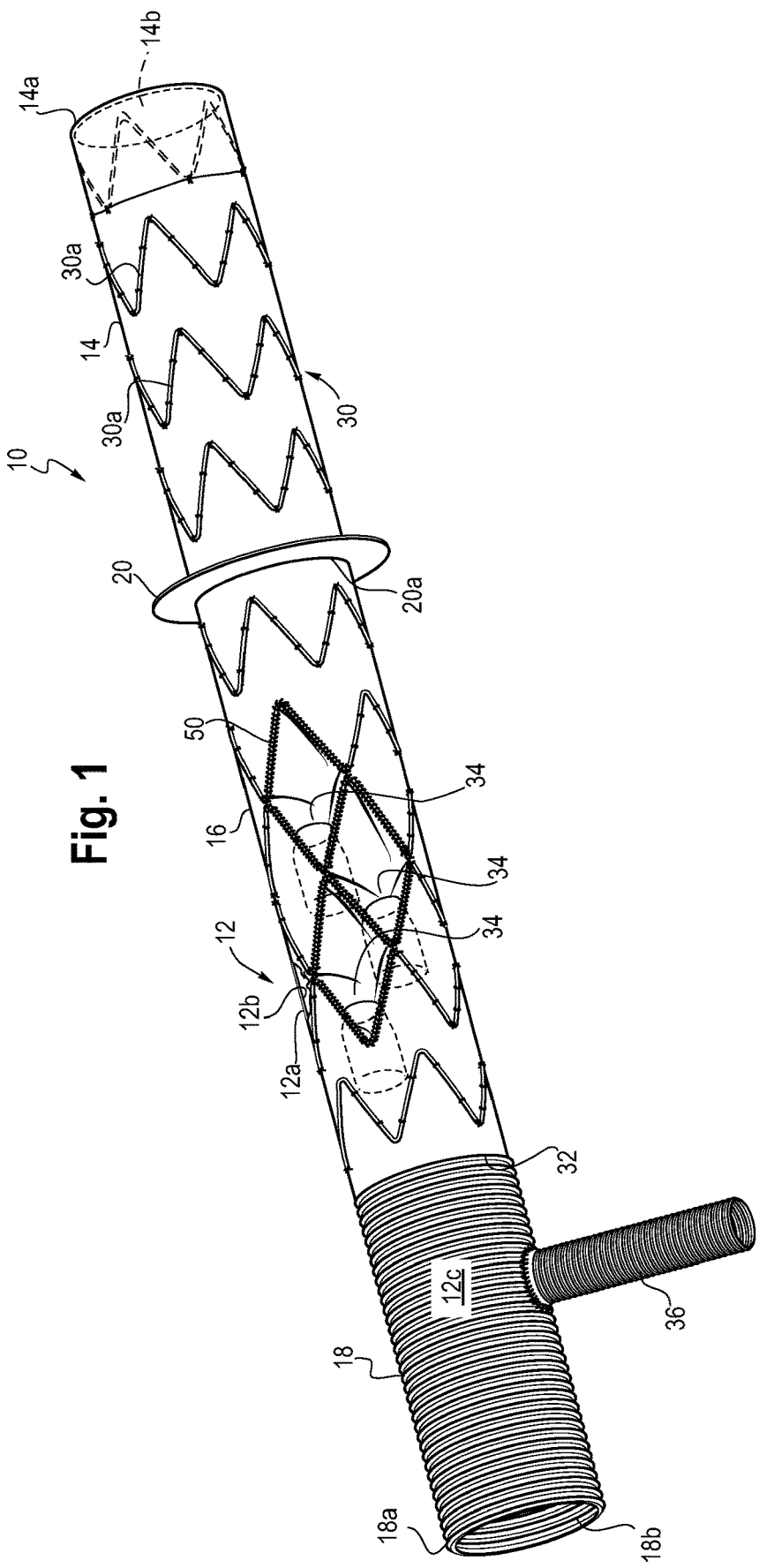
FIG. 1 shows a perspective view of a first example of an endoluminal prosthesis with internal bridging branches.

Unless defined otherwise, all technical and scientific terms used herein have the same meaning as commonly understood to one of ordinary skill in the art to which this invention belongs.

The term "distal" means a location or direction that is, or a portion of a device that when implanted is further downstream in the direction of or with respect to blood flow. In the case of aortic intervention, distal means a location further away from the heart. The distal end of a device for aortic intervention may also be referred to as an inferior end.

The term "proximal" means a location or direction that is, or a portion of a device that when implanted is further upstream in the direction of or with respect to blood flow. In the case of aortic intervention, proximal means a location closer to the heart. The proximal end may also be referred to a superior end.

The term "fenestration" means an opening provided through a surface of a prosthesis from the interior of the prosthesis to the exterior of the prostheses and may have a variety of geometries, including circular, semi-circular, oval, oblong, as well as other geometries.

The term "biocompatible" refers to a material that is substantially non-toxic in the in vivo environment of its intended use, and that is not substantially rejected by the patient's physiological system (i.e., is non-antigenic). Examples of biocompatible materials from which textile graft material can be formed include, without limitation, polyesters, such as polyethylene terephthalate; fluorinated polymers, such as polytetrafluoroethylene (PTFE) and fibers of expanded PTFE, and polyurethanes. In addition, materials that are not inherently biocompatible may be subjected to surface modifications in order to render the materials biocompatible. Examples of surface modifications include graft polymerization of biocompatible polymers on the materials surface, coating of the surface with a cross-linked biocompatible polymer, chemical modification with biocompatible functional groups, and immobilization of a compatibilizing agent such as heparin or other biocompatible substances. Thus, any fibrous material having sufficient strength to survive in the in vivo environment may be used to form a textile graft, provided the final textile is biocompatible. Fibers suitable for making textile grafts include polyethylene, polypropylene, polyaramids, polyacrylonitrile, nylon, and cellulose, in addition to the polyesters, fluorinated polymers, and polyurethanes as listed above. Furthermore, bioremodelable materials may also be used singly or in combination with the aforementioned polymer materials. The textile may be made of one or more polymers that do not require treatment or modification to be biocompatible. The graft may be constructed from woven multifilament polyester, for example and without limitation, Dacron™, produced by DuPONT. Dacron™ is known to be sufficiently biologically inert, non-biodegradable, and durable to permit safe insertion inside the human body.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "tubular" refers to the general shape of an endoluminal device which allows the module to carry fluid along a distance or fit within a tubular structure such as an artery. Tubular prosthetic devices include single, branched, and bifurcated devices. Tubular may refer to any shape including, but not limited to, tapered, cylindrical, curvilinear, or any combination thereof. A tubular device may have a cross-sectional shape that is, circular, substantially circular or the like. However, it should be understood that the cross-sectional shape is not limited thereto, and other shapes, such as, for example, hexagonal, pentagonal, octagonal, or the like are contemplated. The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompasses any duct (e.g., natural or iatrogenic) within the human body and can include a member selected from the group comprising: blood vessels, respiratory ducts, gastrointestinal ducts, and the like. "Endoluminal device" or "endoluminal prosthesis" thus describes devices that can be placed inside one of these lumens.

The term "branch vessel" refers to a vessel that branches off from a main vessel. Examples are the celiac and renal arteries which are branch vessels to the aorta (i.e., the main vessel in this context). As another example, the hypogastric artery is a branch vessel to the common iliac, which is a main vessel in this context. Thus, it should be seen that "branch vessel" and "main vessel" are relative terms.

"Longitudinally" refers to a direction, position or length substantially parallel with a longitudinal axis of a reference, and is the length-wise component of the helical orientation.

"Circumferentially" refers to a direction, position, or length that encircles a longitudinal axis of reference. The term "circumferential" is not restricted to a full 360° circumferential turn or to a constant radius.

The terms "patient," "subject," and "recipient" as used in this application refer to any animal, especially humans.

FIG. 1 illustrates one example of a prosthesis 10. The prosthesis 10 includes a graft 12 having a tubular body. The graft 12 includes a distal portion 14, a middle portion 16, and a proximal portion 18.

The distal portion 14 includes a distal end 14a having a distal opening 14b. The proximal portion 18 includes a proximal end 18a having a proximal opening 18b. The middle portion 16 extends from the distal portion 14 to the proximal portion 18.

The graft 12 is configured as a tubular member having a substantially cylindrical shape, and includes an inner surface 12a and an outer surface 12b. The inner surface 12a thereby delimits a lumen 12c extending from the proximal end 18a to the distal end 14a. The lumen 12c extends longitudinally through the graft 12, and is configured to allow fluid to pass therethrough, such as blood.

The graft 12 may further include a collar 20 disposed at a junction 20a at the intersection between the distal portion 14 and the middle portion 16. The collar 20 is configured for being sutured to the descending aorta to create an anastomosis between the graft and the descending aorta. The collar 20 may project radially from the outer surface 12b of the graft, having the shape of an annular flange. The collar 20 may have a fixed shape to project radially outward from the graft 12. Alternatively, the collar 20 may be formed from excess graft material that projects radially outward in response to relative longitudinal compression of the distal portion 14 toward the middle portion 16, such that this compression will cause the graft material to be pushed outward to form the collar 20.

The graft 12 may further include at least one support structure 30, such as a stent. The support structure 30 may be in the form of a single, unitary, monolithic structure, or it may be in the form of multiple individual structures. In one form, the support structure 30 is a plurality of Z-stents 30a that may be radially compressed into a delivery configuration, where the stents 30a are biased radially outward, and will expand radially outward in response to removing a radial retention mechanism, such as a sheath or diameter-reducing ties.

The support structure 30 may be disposed along the distal portion 14 along substantially the entire length of the distal portion 14. The support structure 30 may also be disposed along the middle portion 16 along substantially the entire length of the middle portion 16.

The proximal portion 18 may be free from any additional support structure such as stents. The middle portion 16 may transition to the proximal portion 18 at a junction 32. The middle portion 16 may be made from a different graft material than the proximal portion 18, with the junction 32 being the transition between different graft materials. In one form, the proximal portion may be Dacron.

The middle portion 16 may include a plurality of passageways 34 disposed through the graft 12 to permit fluid to pass therethrough from the lumen 12c to an area outside of the graft 12. The passageways 34 may also be referred to as fenestrations.

In one example, there are three passageways 34 disposed in the middle portion 16. The passageways 34 may be arranged adjacent each other and on the same circumferential side of the graft 12. These three passageways 34 may be used to communicate with the innominate, left common carotid and left subclavian arteries (the branch vessels).

The passageways 34 may be configured to mate with additional prostheses to communicate with the branch vessels. The passageways 34 will be described in further detail below.

The proximal portion 18 may further include a perfusion side branch 36. The perfusion side branch 36 may be used for antegrade perfusion during repair of the ascending aorta. The perfusion side branch 36 extends radially outward from the proximal portion 18 and provides fluid communication with the lumen 12c.

As shown in FIG. 2, the prosthesis 10 may further include a plurality of bridging branches 40 disposed respectively at each of the passageways 34. The bridging branches 40 each have an inner opening 40a and an outer opening 40b with a lumen 40c extending from the inner opening 40a to the outer opening 40b. The bridging branches 40 provide fluid communication from the inner opening 40a to the outer opening 40b via the lumen 40c. With the bridging branches 40 disposed at the passageways 34, the bridging branches thereby provide fluid communication from within the lumen 12c of the graft 12 to the exterior of the graft through the outer openings 40b.

In one form, the passageways 34 include a support structure 50, shown in FIG. 1, attached to the body of the graft 12. The support structure 50 may have a diamond shape, and may be a single unitary structure of a combination of individual structures. The support structure 50 may be used to keep the passageway 34 open, and may also be used to attach the bridging branch to the body of the graft 12. The support structure 50 may have portions of adjacent stents of the support structure 30.

In one form, as shown in FIG. 2, the bridging branches 40 may be attached to the middle portion 16 of the graft 12 such that the bridging branches 40 are disposed internally within the graft 12. This arrangement may be referred to as internal branches. In this approach, the outer end 40b of the bridging branch 40 may correspond to the location of the support structure 50 of the passageway 34, with the inner end 40a being disposed within the lumen 12c of the graft 12. In this approach, fluid in the lumen 12c may enter the bridging branch 40 within the lumen 12c, and may pass through the outer end 40b at the location of the support structure 50.

In another form as schematically shown in FIG. 3, the bridging branches 40 may be attached to the middle portion 16 of the graft 12 such that the bridging branches 40 are disposed externally outside the lumen 12c of the graft 12. This arrangement may be referred to as external branches. In this approach, the inner end 40a of the bridging branch 40 may correspond to the location of the support structure 50 of the passageway 34, with the outer end 40b being disposed radially away from the body of the graft 12. In this approach, fluid in the lumen 12c may enter the bridging branch 40 at the location of the support structure 50 in the sidewall of the graft 12, and may pass through the outer end 40b at a location radially away from the sidewall of the graft 12 and the support structure 50.

As shown in FIGS. 4 and 5, the bridging branches 40 may include support structure 52 to maintain a generally tubular shape to remain open and allowing fluid to flow therethrough. The support structure 52 may include a stent ring 52a disposed at the ends of the branches 40, along with a strut 52b that extends longitudinally along the length of the bridging branch 40 from end to end and between the rings 52a. In one approach, one of the rings 52a at the end of the bridging branch may be replaced by the support structure 50 of the passageway 34, with the strut 52b extending between the ring 52a and the support structure 50, as shown in FIG. 4.

The bridging branches 40 may also be arranged to be pivotable relative to the body of the graft 12, as shown in FIG. 5. With reference to the external branch arrangement, the inner ends 40a of the bridging branches 40 may be attached to the support structure 50 via an additional graft material 54. The material 54 may be sewn to the support structure 50, and may extend to the support ting 52a of the branch. The material 54 may be free from support structure extending between the support structure 50 and the ring 52a, thereby remaining generally flexible and allowing the branch 40 to pivot at the location of the passageway 34 when the material 54 bends and flexes.

The bridging branches 40 of the external branch arrangement may also include support structure in the form of a pair of 2-point stents 52c rather than longitudinal struts 52b.

The above described bridging branches 40 may be used to mate with additional prostheses that also mate with the branch vessels, as further described below.

With reference to FIG. 6, the prosthesis 10 may further include a plurality of pre-loaded catheters 60. The catheters 60 may be used to position and support the bridging branches 40, as well as to receive and route wires used to deliver and deploy the additional prostheses for cannulating the branch vessels. The catheters 60 are preloaded, such that they are disposed within the prosthesis 10 prior to the prostheses 10 being deployed within the vasculature.

The catheters 60 have an elongate tubular shape having a proximal end 60a and a distal end 60b and a lumen extending from the proximal end 60a to the distal end 60b. The proximal end 60a and distal end 60b are each open, allowing a wire to be routed through the catheter 60 and out of each end 60a, 60b.

The proximal end 60a is preferably disposed proximally from the proximal end 18a of the graft 12, such that the catheters 60 extend out of the proximal end 18a, providing access to a wire that extends through the catheter 60. The distal end 60b is preferably disposed near the outer end 40b of the bridging branch 40, such that the catheters 60 extend at least partially into and through the bridging branches 40. The distal end 60b may extend out of the outer end 40b of the bridging branches 40.

The catheters 60 are movable relative to the graft 12, such that they may be retracted proximally out of the graft 12, or extended distally out of the outer end 40b of the bridging branches 40.

As will be described in further detail below, the catheters 60 may be used to receive a wire into the distal end 60b, with the wire being routed proximally out of the proximal end 60a, thereby assisting in routing the wire through the bridging branches 40 without damaging the bridging branches 40.

With reference to FIG. 7, additional prostheses may be attached and mated with the bridging branches 40 of the prosthesis 10 to provide endovascular repair. Thus, a plurality of bridging grafts 70 may be provided with the prosthesis 10, with the grafts 70 being sized and configured to mate with the bridging branches 40. The bridging grafts 70 may be referred to as bridging grafts, branch extensions, or graft extensions. For purposes of discussion, the bridging grafts 70 will be referred to as graft extensions 70 so as not to be confused with the bridging branches 40.

The graft extensions 70 may have a tubular structure of graft material and include an inner end 70a and an outer end 70b with a lumen 70c extending from the inner end 70a to the outer end 70b. The graft extensions 70 may include a support structure 72, such as stents, that operate to bias the graft radially outward and into engagement with corresponding structure or the wall of a branch vessel or other body vessel in which they are disposed. The support structure 72 may be in the form of a single unitary structure, or may be a combination of multiple individual structures.

The support structure 72 is preferably biased radially outward when compressed, such that when the graft extension 70 is delivered in compressed configuration and released from its compression, the graft extension 70 will expand radially outward into engagement with corresponding structure or vessel wall in which the graft extension 70 is disposed.

The support structure 72 may include a seal stent 72a at the inner end 70a of the graft extension 70, such that the seal stent 72a is disposed on an interior surface of the graft extension 70, with the exterior surface of the graft extension 70 being generally smooth. The outer end 70b may also include a seal stent 72b that is similarly disposed on the interior surface of the graft extension 70.

The graft extensions 70 may be housed in a delivery system where the graft extensions 70 are compressed radially and have a generally low profile, such that they may be inserted over a wire to a target location. Delivery systems for tubular stent-grafts are known in the art, and such delivery systems may be used for the delivery of this graft extension 70. For example, the system may include a support catheter on which the graft extension is mounted, and may include an outer sheath that keeps the graft extension radially compressed. The sheath may be a retractable tubular sheath, or may be a peel-away sheath. For illustration purposes, the graft extensions 70 are shown without their corresponding delivery system.

To deliver the graft extensions 70 into engagement with the bridging branches 40 and the corresponding branch vessel, a plurality of wires 74 (FIG. 6) may be provided. The wires 74 may also be referred to as SAT wires ("supra aortic trunk" wires). The wires 74 are preferably delivered into the patient's body through micropuncture of the right and left brachial arteries and left common carotid arteries, and may be guided via ultrasound. The wires 74 may be delivered into the arch supra aortic trunk, and out of the branch vessels.

During deployment of the prosthesis 10 into the aorta, the wires 74 may each be routed into the distal ends 60b of the preloaded catheters 60 and further routed out of the proximal ends 60a. With the wires 74 extending through the catheters 60, the catheters 60 may be removed/retracted, leaving the wires 74 in place. FIG. 6 illustrates an example of the wires 74 having been inserted into the distal ends 60b of the catheters 60 from the branch vessels (not shown in FIG. 6).

The wires 74 will therefore extend through the bridging branches 40 from the exterior of the prosthesis 10 near the branch vessels and out of the proximal end 12a of the prosthesis 12. The graft extensions 70 can therefore be delivered over the wires 74, and will be routed through the bridging branches 40 and along the wires 74 into the branch vessels. The graft extensions 70 will therefore extend from the bridging branches 40 into the branch vessels, and can expand outward into engagement with the bridging branches 40 and the branch vessels.

In one example, as shown in FIG. 8, the wires 74 may be provided along with the prosthesis 10 in a preloaded manner. In this approach, the wires 74 are preloaded in the prosthesis 10 within the preloaded catheters 60, meaning that the wires 74 are loaded within the catheters 60 and the prosthesis 10 prior to delivery and deployment within the patient's body. In this approach, the wires 74 are not inserted into the body via micro puncture and routed to the branch vessels. Rather, the wires 74 are present in the prosthesis and routed into the branch vessels after transection of the aorta. This approach can be less invasive that the previously described approach utilizing micropuncture. After being extended out of the catheter 60, the position of the wires 74 would resemble FIG. 6.

Figure 9A:
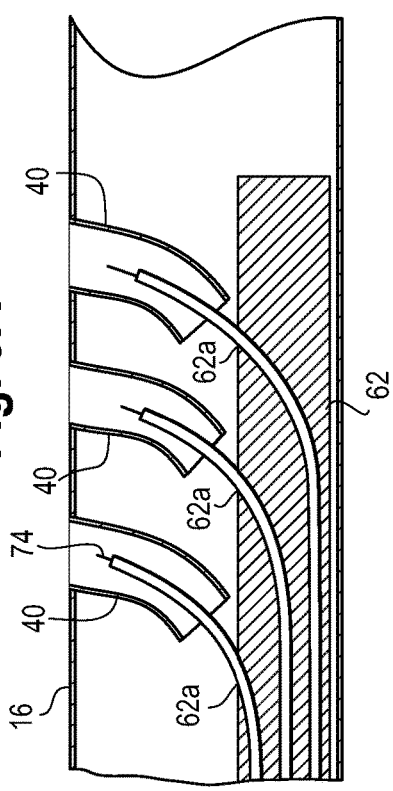
FIGS. 9A and 9B show details of a tri-lumen pusher for delivering graft extensions.
Figure 9B:
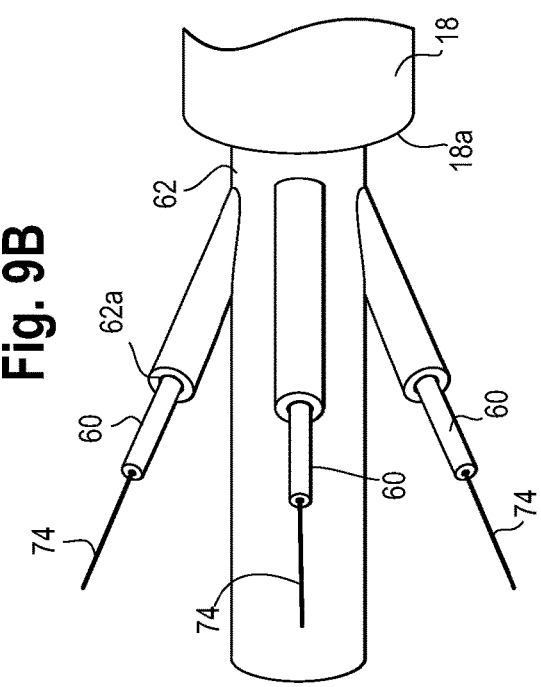

As described above, the catheters 60 may be preloaded within the prosthesis 10. With reference to FIGS. 9A and 9B, the catheters 60 may be loaded within a tri-lumen pusher 62 that may be part of the delivery system for the prosthesis 10. The pusher 62 may include entry ports 62a adjacent the proximal end 18a of the prosthesis 10 and exit ports 62b located at each of the bridging branches 40.

The catheters 60 may extend through the tri-lumen pusher 62 such that the distal ends 60b are disposed at each of the corresponding bridging branches 40. The wires 74 may each extend through the catheters 60, with the distal ends of the wires being disposed short of the ends of the catheters 60 or extending slightly beyond the ends of the catheters 60 (as shown in FIG. 9a). The wires 74 are movable relative to the catheters 60, such that the catheters 60 operate as a guide for the wires 74.

In this approach, the ostiums of the branch vessels may be visualized when the prosthesis 10 is deployed within the aorta. The wires 74 may be advanced out of the catheters 60 and into each of the corresponding branch vessels. The catheters 60 may then be advanced into the branch vessels over the wires 74. When it is time to deliver and deploy the graft extensions 70, the catheters 60 may be retracted out of the prosthesis 10 and the graft extensions 70 may be delivered over the wires 74 that remain within the ostiums.

The above described structure of the prosthesis 10 and related structure has been generally described in its deployed configuration. However, the prosthesis 10 may have a delivery configuration for various portions of the prosthesis during delivery and deployment of the prosthesis 10 during the aortic repair procedure.

For example, in one form, the distal portion 14 of the graft 12 may have a compressed delivery configuration. The distal portion 14 is intended to be delivered into the descending aorta into a true lumen of aortic dissection when present. To deliver the distal portion 14 into the descending aorta, the distal portion 14 may be delivered over a wire that has been introduced via a traditional transfemoral approach, with the wire inserted via femoral puncture and advanced into the descending aorta.

As shown in FIG. 10, the prosthesis 10 may therefore include a restraining sheath 76 that surrounds and compresses the distal portion 14 therein. The restraining sheath 76 may be a peel away sheath or a push/pull sheath. In the peel away sheath form, the distal portion 14 may be inserted over the femoral wire into the descending aorta, and the sheath 76 may be peeled away, allowing the distal portion 14 to expand radially outward into engagement with the vessel wall. In the push/pull sheath form, the distal portion 14 may be advanced over the femoral wire, and the sheath 76 may then be pushed distally away from the prosthesis, allowing the distal portion 14 to expand radially outward, and the sheath 76 may then be retracted proximally back through the prosthesis 10 because the distal portion has expanded.

With reference to FIG. 11, the distal portion 14 may be compressed radially via the use of diameter-reducing ties 77. Diameter-reducing ties are known in the art, and typically include a plurality of loops sewn into the graft 12 that are held together via trigger wires. Retracting the trigger wires allows the loops to separate from each other and the graft 12 may expand.

As shown in FIG. 11, the middle portion 16 can likewise be compressed radially through the use of the diameter-reducing ties 72. The use of diameter-reducing ties allows for the passageways 34 and bridging branches 40 to be visualized and accessed while the middle portion 16 remains in the compressed configuration. Thus, the wires 74 may be inserted into the passageways 34 or bridging branches 40 via the catheters 60, or may be extended out of the catheters 60 into the branch vessels, while the middle portion 16 remains compressed. With the middle portion 16 of the prosthesis 10 compressed, the ostiums of the branch vessels may be more easily visualized and accessed. Once the wires 74 and/or catheters 60 have been inserted into the branch vessels, the diameter-reducing ties of the middle portion 16 may be released, allowing the middle portion to expand outwardly into engagement with the vessel wall.

Having described the structure of the prosthesis 10 and corresponding components, exemplary methods for delivering and deploying the prosthesis 10 and corresponding components will now be described.

Initially, the patient may be placed on cardiopulmonary bypass in a manner known in the art. The descending and ascending aorta may be transected in a traditional manner, thereby providing access to the aortic arch and the branch vessels, as well as the descending and ascending aorta.

A femoral wire 75 may be introduced into the descending aorta via femoral puncture in a traditional manner. The femoral wire 75 will be inserted into the patient's body through femoral puncture and routed into the descending aorta to a location near the branch vessels and a desired location for the distal portion 14 of the prosthesis 10.

The SAT wires 74 may be introduced via micropuncture of the left and right brachial arteries and left common ceratoid artery. The wires 74 may be guided by ultrasound and routed to the arch supra aortic trunk, such that the wires 74 will extend out of the branch vessels, in particular the innominate trunk (IT), the left common carotid (LCC) artery, and the left subclavian artery (LSA). With the ends of the wires 74 and 75 disposed within the aortic arch, the wires 74 and 75 are accessible to the surgeon for further use with the prosthesis 10.

The surgeon may institute cerebral perfusion through the right axillary and left common carotid arteries.

Figure 12:
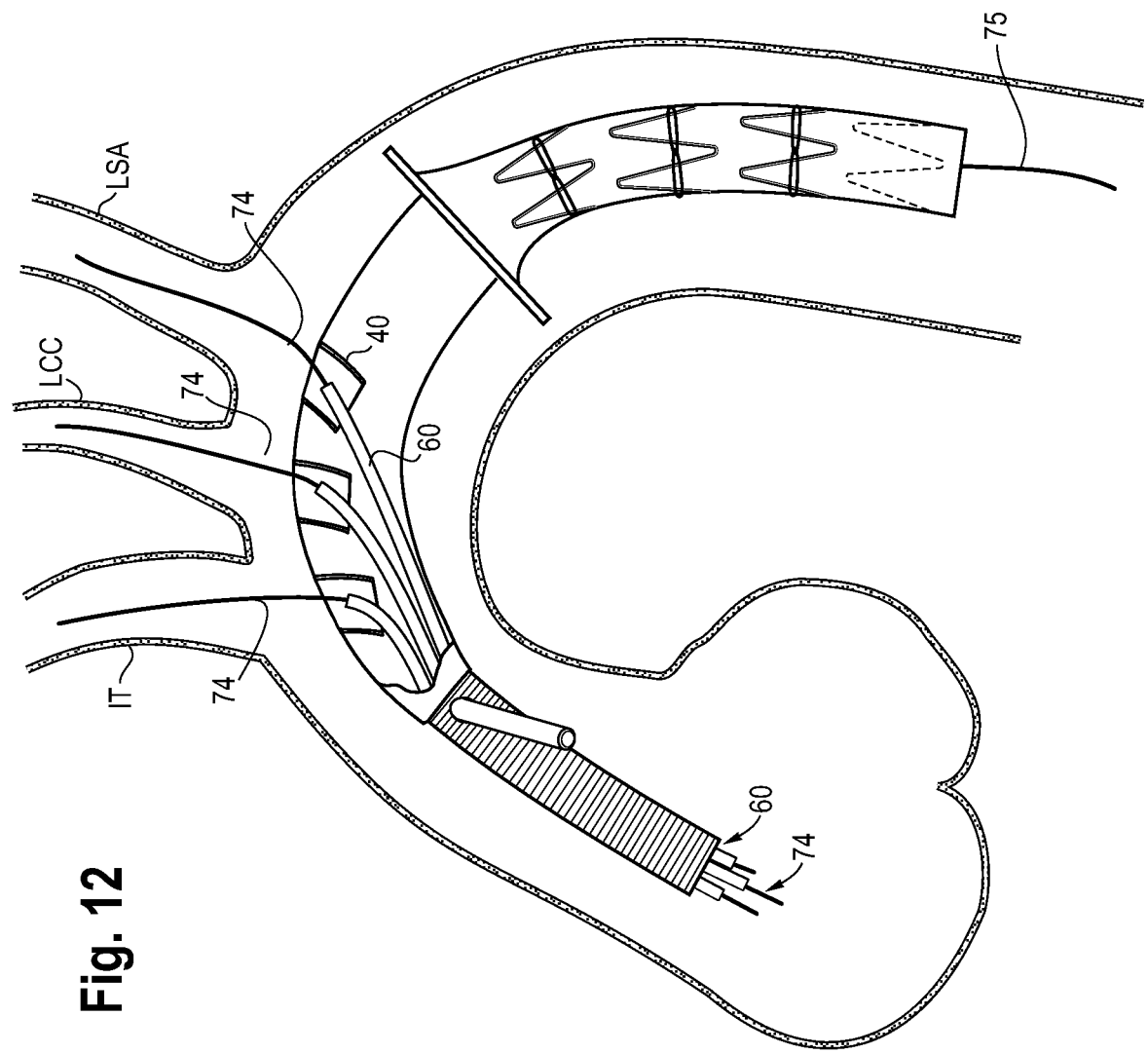

As shown in FIG. 12, with access to the SAT wires 74, the wires 74 may be backloaded into the respective preloaded catheters 60, such that the wires 74 will enter the distal end 60b of each of the preloaded catheters 60, which are preloaded within the prosthesis 10 and extend through the bridging branches 34. Thus, the wires 74 may be loaded into the catheters 60 and routed out of the proximal ends of the catheters 60, providing access to the ends of the wires 74 after they have been loaded into the catheters 60. The catheters 60 operate to protect the internal surfaces of the prosthesis 10, such that the wires 74 will not puncture or damage the walls of the prosthesis 10.

The prosthesis 10 may then be delivered into the descending aorta, as shown in FIG. 12, in the true lumen of dissection in the case of aortic dissection. In particular, the prosthesis 10 may be part of a delivery system where the distal portion 14 and middle portion 16 are in a radially compressed state. The compressed distal portion 14 may be inserted into the descending aorta over the femoral wire 75.

Figure 13:
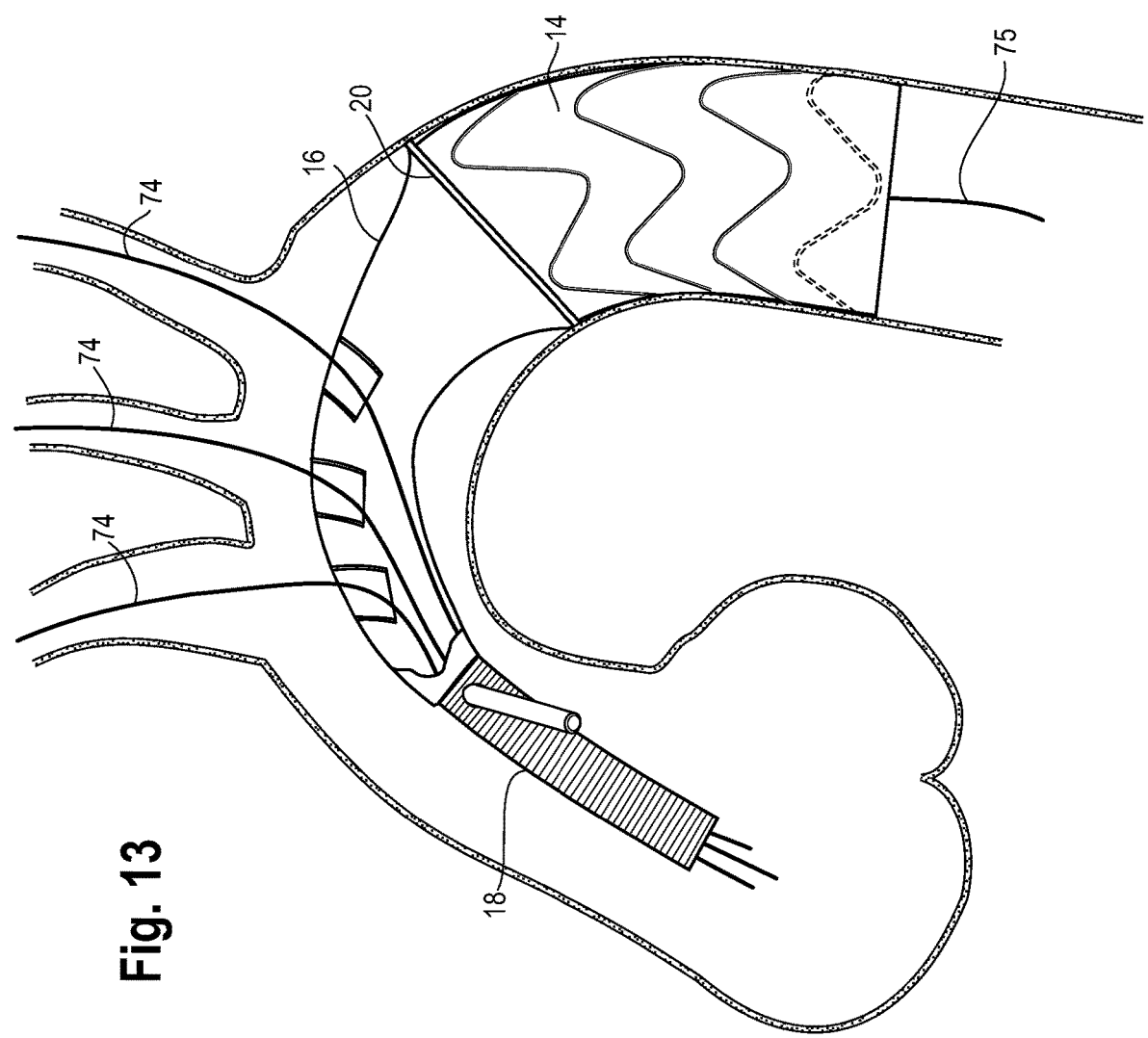

As shown in FIG. 13, with the distal portion 14 in the desired location, the distal portion 14 may be allowed to expand into engagement with the vessel wall. In the case of a peel-away sheath 76, the sheath 76 may be peeled-away, exposing the distal portion 14 and allowing the support structure 30 to cause the distal portion 14 to expand. In the case of a push-pull sheath 76, the sheath may be advanced distally to expose the distal portion 14 and allow it to expand, and then retracted back through the prosthesis 10 after the distal portion 14 has expanded. In the case of diameter-reducing ties 72, the ties 72 may be released, allowing the distal portion 14 to expand.

After the distal portion 14 has expanded, the collar 20 may be sutured to the aortic wall to create an anastomosis. At this point, the prosthesis 10 is "frozen" at the distal portion 14 and the collar 20, such that the prosthesis 10 will stay in place. The anastomosis created by suturing the collar 20 blocks flow that may occur outside of the prosthesis 10 once deployed.

As described above, the wires 74 have been routed through the catheters 60 and are accessible to the surgeon at the proximal end of the prosthesis 10. The wires 74 provide a routing function for the graft extensions 70 that will be deployed through the bridging branches 40.

Figure 14:
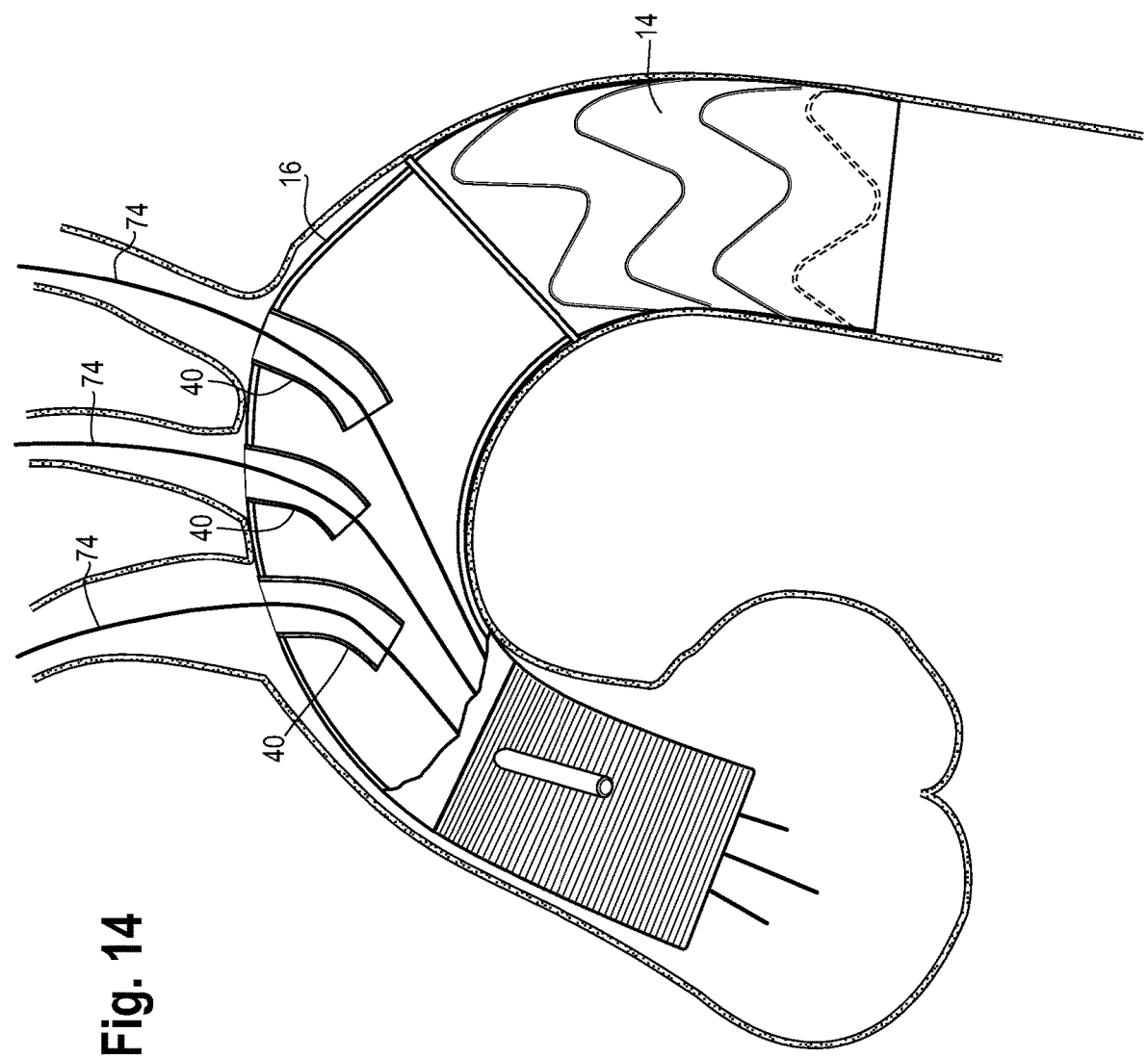

Accordingly, as shown in FIG. 14, the middle portion 16 of the prosthesis 10 may be released from its radially compressed delivery state by releasing the diameter-reducing ties 72. The middle portion 16 will expand radially into engagement with the vessel wall. Unlike the distal portion 14, suturing or creating an anastomosis for the middle portion 16 may not be performed.

As shown in FIG. 14, with the middle portion 16 expanded, the catheters 60 may be retracted proximally out of the prosthesis 10, leaving the wires 74 in place. The graft extensions 70 may then be advanced over the wires 74 into the corresponding branch vessels.

Figure 15:
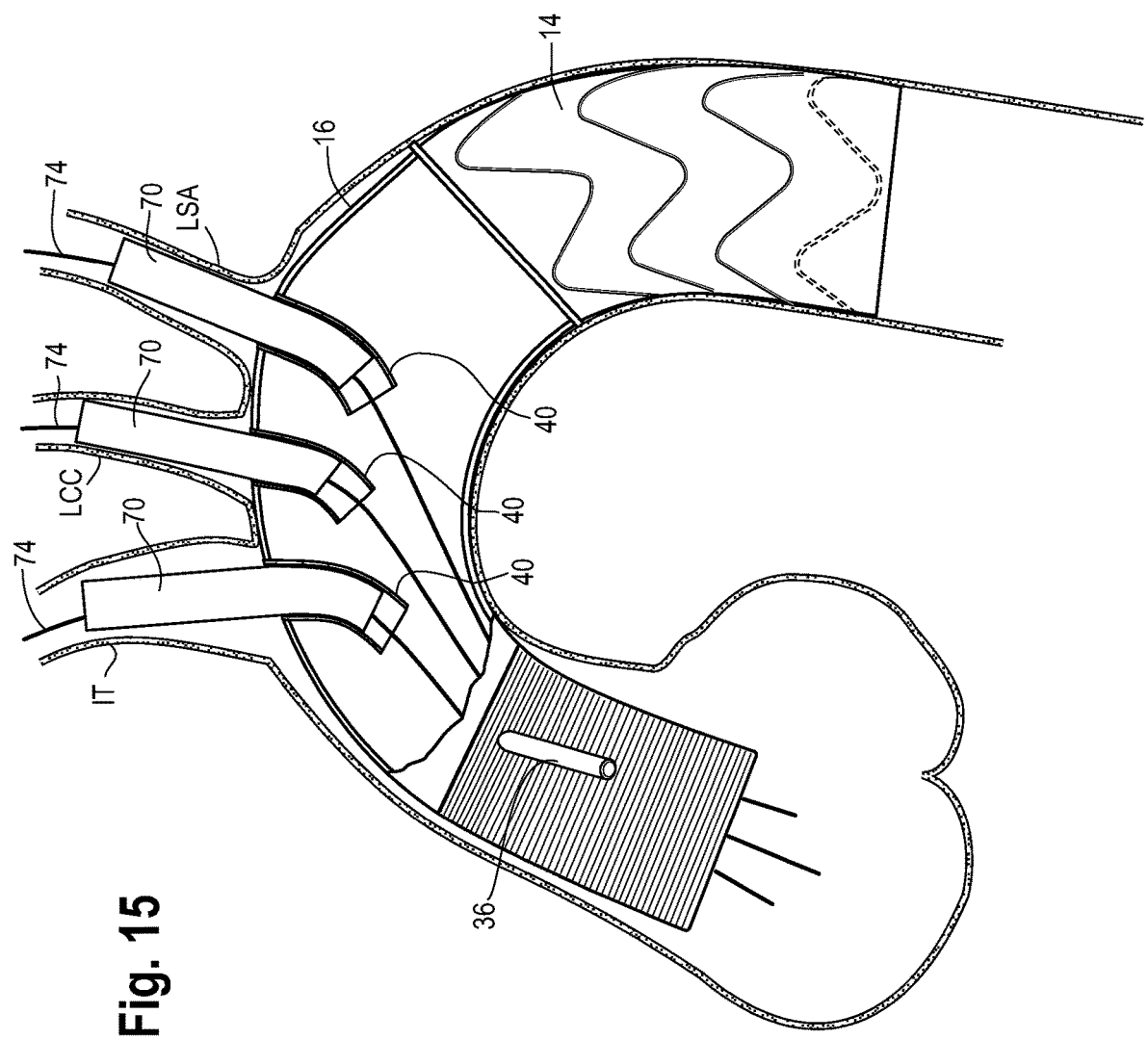

With reference to FIG. 15, more particularly, the graft extension 70 for the LSA may be advanced first. The graft extension 70 has a compressed delivery state, and may be advanced over the wire 74 corresponding to the LSA. The graft extension 70 may be extending through the bridging branch 40 corresponding to the LSA over the corresponding wire 74. Once the graft extension 70 is in its desired location, such as in a position where the graft extension 70 overlaps the bridging branch and also extends into the LSA, the graft extension 70 may be released. The graft extension 70 is preferably delivered within a sheath, such that deploying the graft extension 70 involves retracting and/or peeling away the sheath, allowing the graft extension 70 to expand. The graft extension 70 at this point is deployed and held in place by its radially outward engagement with the bridging branch 40 and the vessel wall.

Next, the perfusion cannula (not shown) used for cerebral perfusion may be retracted out of the LCC, with the LCC being the next branch vessel for delivery of a graft extension 70 thereto. After retrieving the perfusion cannula, the graft extension 70 for the LCC will be delivered over the wire 74 and through the bridging branch 40 that corresponds to the LCC. The graft extension 70 will then be expanded from its delivery state to its deployed state in the manner described above. With the graft extension 70 deployed within the LCC, the perfusion cannula will be repositioned into the graft extension 70 of the LCC.

Next, the graft extension 70 for the IT will be delivered over the wire 74 and through the bridging branch 40 corresponding to the IT. The graft extension 70 will be released and expanded as described above. At this point, each of the branch vessels have received their corresponding graft extension 70, and fluid communication from the interior of the prosthesis 10 to the branch vessels is possible. The wires 74 may be removed after the graft extensions 70 have been deployed.

The proximal portion 18 of the prosthesis 10 is subsequently deployed. More particularly, the proximal portion 18, which may be a wrapped Dacron material, may be unwrapped. The proximal portion 18 may then be flushed. The perfusion cannula extending into the LCC graft extension 70 may be retrieved, and the proximal portion 18 may be clamped.

The side branch 36 extending from the proximal portion 18 may then be flushed, and the perfusion cannula is inserted into the side branch 36. Antegrade perfusion may then be started through the side branch, with the perfusion passing through the interior of the prosthesis 10.

The proximal portion 18 may then be sutured to the ascending aorta and the proximal ascending repair may be completed. The proximal portion 18 may be unclamped, the perfusion cannula may be removed from the side branch and closed in a traditional manner, and the patient may be taken off bypass in a traditional manner.

This method allows for a reduction in the number of suturing steps and anastomoses that are created during the aortic repair. The delivery of graft extensions over the wires rather than creating anastomoses greatly reduces the amount of time in the procedure, increasing the likelihood of successful repair and reducing the time spent on bypass.

Figure 15A:
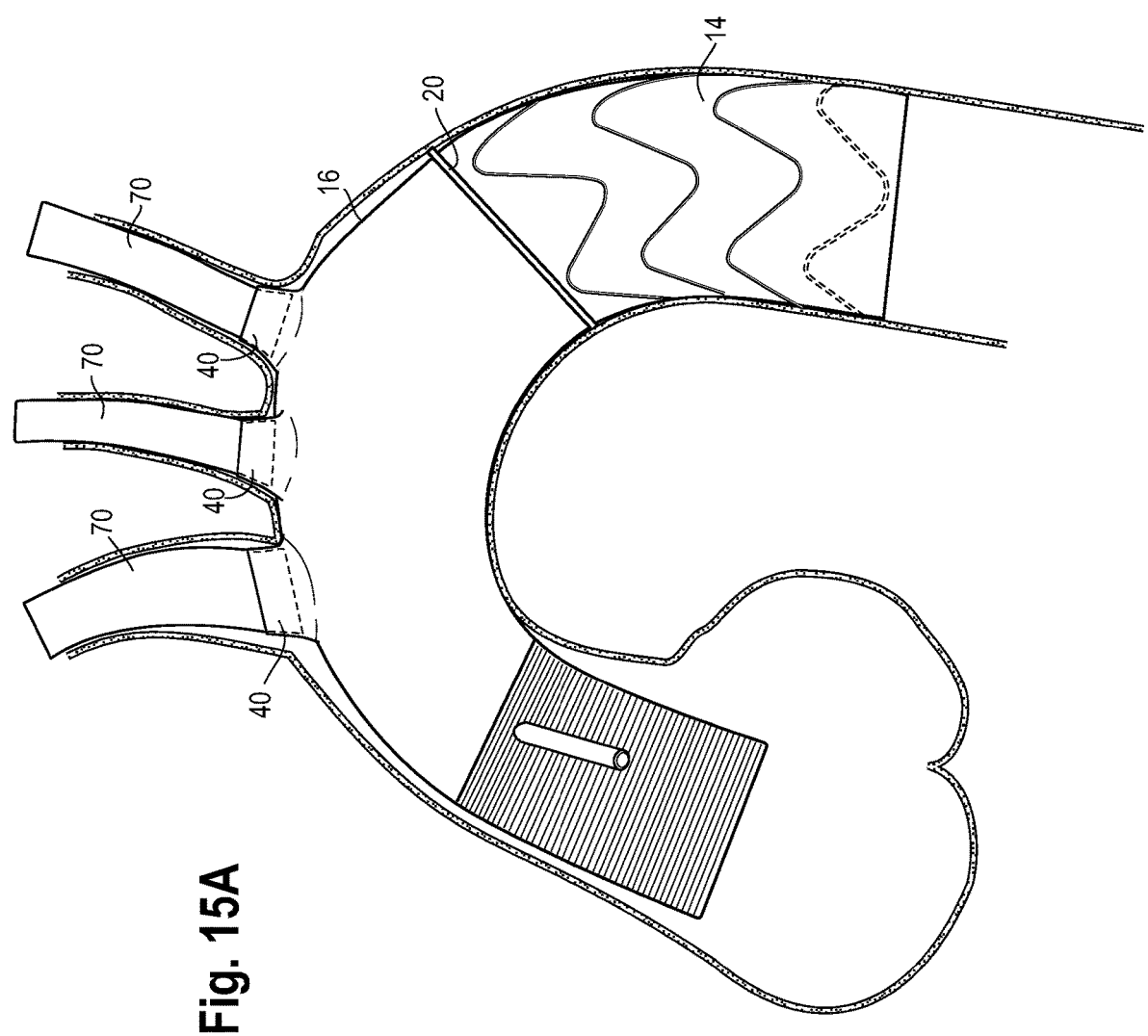

The above method may be performed for either example of bridging branches 40 (either the branches 40 that are generally internal or the branches 40 that are external and capable of the pivoting). In the case of pivoting branches 40, the branches 40 may pivot proximally, distally, or laterally during the deployment of the graft extensions 70 to accommodate variations in patient anatomy. An example of the graft extensions 70 being deployed within the external pivoting branches 40 is shown in FIG. 15A.

In another approach, the prosthesis 10 includes the preloaded catheters 60 along with the wires 74 for the branch vessels being preloaded in the catheters 60 rather than extending down from the branch vessels. For this type of prosthesis 10, the method may be modified.

In this approach, the micropuncture and routing of wires through the vasculature and out of the branch vessels may be excluded. This is possible because the wires 74 are already disposed within the catheter 60. However, this approach therefore includes additional steps related to delivering the wires into the branch vessels to allow for the graft extensions 70 to be deployed over the wires.

Figure 16:
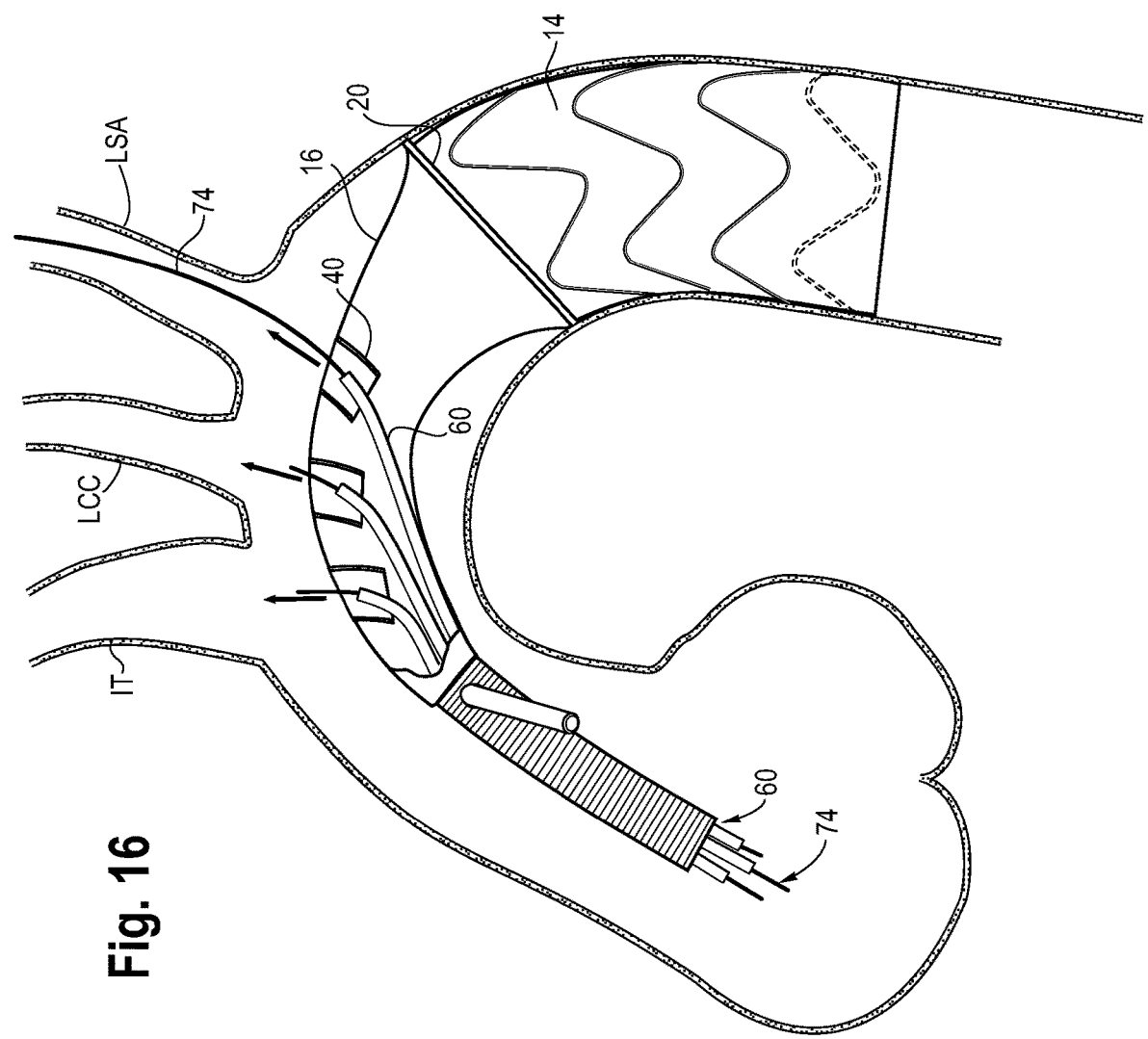

Thus, as shown in FIG. 16, after the collar 20 is sutured to the aortic wall as described above, the wires 74 will be delivered into the branch vessels. More particularly, the wires 74 are extended out of the distal ends of the catheters 60 into the IT, LCC, and LSA. The precise order in which the wires 74 are extended into the branch vessels may vary.

Figure 17:
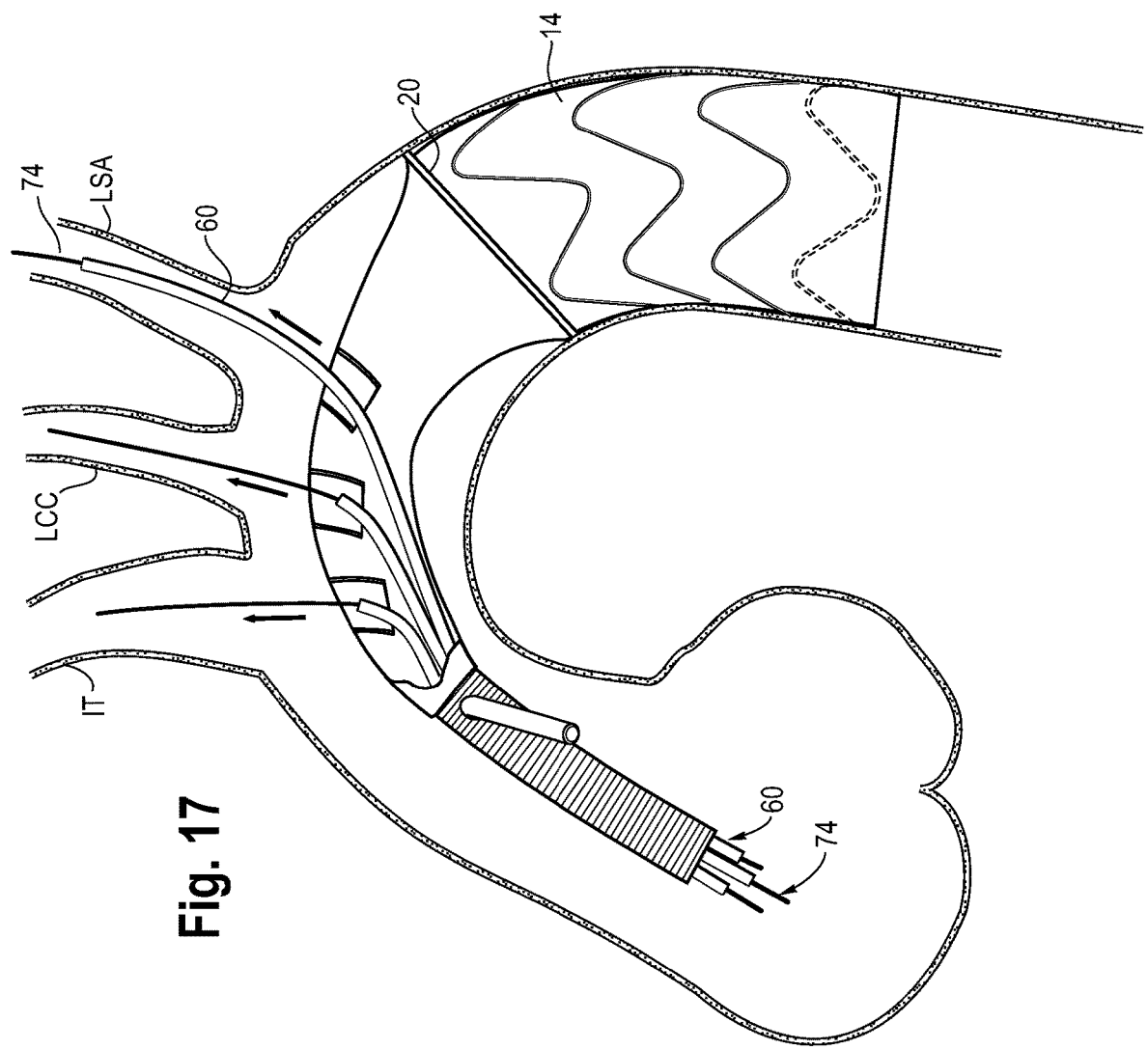

As shown in FIG. 17, after the wires 74 have been extended into the branch vessels, the catheters 60 may be extended over the wires 74 into the branch vessels as well. The precise order in which the catheters 60 are delivered over the wires 74 can vary.

In one approach, each of the wires 74 are advanced prior to the catheters 60 being advanced. In another approach, one of the wires 74 may be advanced into a branch vessel, followed by one of the catheters 60. It will be appreciated that various modifications to the order and number of wires advanced relative to catheters can be modified or adjusted to fit the needs of the surgeon and/or patient.

As shown in FIG. 18, after the wires 74 and catheters 60 have been delivered into the branch vessels, the middle portion 16 may be expanded by releasing the diameter-reducing ties as described above. After the middle portion 16 has expanded, the catheters 60 may be retracted out of the prosthesis 10, leaving the wires 74 extending from the branch vessels through the prosthesis 10, similar to the illustration of FIG. 14. The previously described method for delivering and deploying the graft extensions 70 over the wires 74 (and for both the internal and external bridging branches 40) and finishing the aortic repair may remain the same as previously described. The method using the preloaded wires 74 may be used with any of the bridging branches 40 described above.

Throughout this specification various indications have been given as to preferred and alternative examples and aspects of the invention. However, the foregoing detailed description is to be regarded as illustrative rather than limiting and the invention is not limited to any one of the provided aspects. It should be understood that it is the appended claims, including all equivalents that are intended to define the spirit and scope of this invention.

What is claimed is:

1. An endoluminal prosthesis system for being deployed in a patient's aorta near the heart, the system comprising:
    a graft having a tubular body with a proximal end and a distal end, where the proximal end is an end configured to be deployed near a patient's heart and the distal end is an end configured to be deployed away from the patient's heart, the tubular body having a lumen extending from the proximal end to the distal end;
    a proximal portion of the graft including the proximal end;
    a distal portion of the graft including the distal end;
    a middle portion of the graft extending from the proximal portion to the distal portion;
    a collar disposed at a junction between the middle portion and the distal portion, the collar having an attached end and a free end, wherein the attached end is attached to an outer surface of the tubular body about a circumference of the tubular body and the free end projects radially away from an outer surface of the tubular body and sized and configured to be sutured to a patient's aorta;
    a plurality of passageways in the middle portion of the graft, wherein the passageways permit fluid communication from the lumen of the graft to an exterior of the graft;
    a plurality of bridging branches, each of the bridging branches respectively disposed at one of the passageways, each of the bridging branches having an inner opening and an outer opening, wherein the bridging branches provide fluid communication from the lumen of the graft to the exterior of the graft, wherein at least a portion of the bridging branches extends within the lumen of the tubular body; and
    a plurality of bridging grafts, each of the bridging grafts sized and arranged to mate respectively with one of the bridging branches.

2. The system of claim 1, wherein the middle portion of the graft is stented.

3. The system of claim 2, wherein the middle portion includes a plurality of reinforcing members, each of the reinforcing members respectively surrounding one of the passageways.

4. The system of claim 2, wherein the proximal portion is unstented and includes a side branch extending radially outward from the proximal portion and providing fluid communication into the lumen of the graft.

5. The system of claim 1, further comprising a plurality of catheters extending into the proximal end, each of the catheters extending into a respective one of the plurality of bridging branches, wherein the catheters are moveable out of the bridging branches.

6. The system of claim 1, further comprising a plurality of wires sized and configured to be extended through the bridging branches and the proximal end.

7. The system of claim 1, wherein the outer opening of each of the bridging branches is attached at a sidewall of the middle portion, and the inner opening of each of the bridging branches is disposed within the lumen of the graft.

8. The system of claim 1, wherein the inner opening of each of the bridging branches is attached at a sidewall of the middle portion, and the outer opening is disposed outside of the lumen of the graft.

9. The system of claim 8, wherein each of the bridging branches is pivotable relative to the tubular body of the graft at an attachment interface between the tubular body and the bridging branch.

10. An endoluminal prosthesis system for being deployed in a patient's aorta near the heart, the system comprising:
    a graft having a tubular body with a proximal end and a distal end, where the proximal end is an end configured to be deployed near a patient's heart and the distal end is an end configured to be deployed away from the patient's heart, the tubular body having a lumen extending from the proximal end to the distal end;
    an unstented proximal portion of the graft including the proximal end;
    a stented distal portion of the graft including the distal end;
    a stented middle portion of the graft extending from the proximal portion to the distal portion;
    a plurality of bridging branches attached to a wall of the tubular graft and disposed within the stented middle portion, each of the bridging branches having an inner opening and an outer opening, wherein the bridging branches provide fluid communication from the lumen of the graft to the exterior of the graft, and wherein the bridging branches are disposed within the lumen of the tubular body; and
    a plurality of preloaded catheters extending through the inner openings of the bridging branches and through the distal end of the graft wherein catheters are preloaded, such that they are disposed within the prosthesis prior to the prosthesis being deployed within the vasculature.

11. The system of claim 10, further comprising a plurality of bridging grafts, each of the bridging grafts being sized and arranged to mate respectively with one of the bridging branches.

12. The system of claim 10, further comprising a plurality of preloaded wires extending into the catheters and configured to be extended out of the catheters and out of the outer opening of the bridging branches.

13. The system of claim 10, wherein the distal portion has a compressed delivery configuration and an expanded deployed configuration, the distal portion being expandable into the deployed configuration separately from the middle portion.

14. The system of claim 10, wherein the middle portion has a compressed delivery configuration and an expanded deployed configuration.

15. The system of claim 10, wherein the inner openings of the bridging branches are disposed inside the lumen.

16. The system of claim 10, wherein the inner openings of the bridging branches are attached to a wall of the middle portion and the bridging branches are pivotable relative to graft.

17. An endoluminal prosthesis for being deployed in a patient's aorta near the heart, the prosthesis comprising:
   a graft having a tubular body with a proximal end and a distal end, where the proximal end is an end configured to be deployed near a patient's heart and the distal end is an end configured to be deployed away from the patient's heart, the tubular body having a lumen extending from the proximal end to the distal end;
   a proximal portion of the graft including the proximal end;
   a distal portion of the graft including the distal end;
   a middle portion of the graft extending from the proximal portion to the distal portion, wherein each of the distal portion and the middle portion is stented and separately expandable from a compressed delivery configuration to an expanded deployed configuration;
   a collar disposed at a junction from the middle portion to the distal portion, the collar having an unattached free end projecting radially from an outer surface of the tubular body and sized and configured to be sutured to a patient's aorta;
   a plurality of passageways in the middle portion of the graft, wherein the passageways permit fluid communication from the lumen of the graft to an exterior of the graft;
   a plurality of bridging branches, each of the bridging branches respectively disposed at one of the passageways, each of the bridging branches having an inner opening and an outer opening and extending inside the tubular body of the graft.

18. The prosthesis of claim 17, wherein each of the bridging branches includes a stent ring to maintain a generally tubular shape.

19. The prosthesis of claim 17, wherein each of the bridging branches is configured to be connected to a tubular graft extension.

20. The prosthesis of claim 17, further including a respective tubular graft extension attached to each of the bridging branches.

21. An endoluminal prosthesis system for being deployed in a patient's aorta near the heart, the system comprising:
   a graft having a tubular body with a proximal end and a distal end, where the proximal end is an end configured to be deployed near a patient's heart and the distal end is an end configured to be deployed away from the patient's heart, the tubular body having a lumen extending from the proximal end to the distal end and an outer surface;
   an unstented proximal portion of the graft including the proximal end;
   a stented distal portion of the graft including the distal end;
   a stented middle portion of the graft extending from the proximal portion to the distal portion;
   a collar disposed at a junction between the middle portion and the distal portion and projecting radially from an outer surface of the tubular body and sized and configured to be sutured to a patient's aorta;
   a plurality of passageways in the middle portion of the graft, wherein the passageways permit fluid communication from the lumen of the graft to an exterior of the graft;
   a plurality of bridging branches, each of the bridging branches respectively disposed at one of the passageways, each of the bridging branches having an inner opening and an outer opening and extending inside the tubular body of the graft, wherein the bridging branches provide fluid communication from the lumen of the graft to the exterior of the graft; and
   a plurality of bridging grafts, each of the bridging grafts sized and arranged to mate respectively with one of the bridging branches.

* * * * *